United States Patent
Gill et al.

(10) Patent No.: US 9,290,851 B2
(45) Date of Patent: Mar. 22, 2016

(54) SPECIFIC 3-ALKYLAMINO-2-HYDROXYSUCCINIC ACIDS AND THEIR SALTS AS CORROSION INHIBITORS FOR FERROUS METALS

(71) Applicant: Ecolab USA, Inc., Naperville, IL (US)

(72) Inventors: Jasbir S. Gill, Naperville, IL (US);
Peter E. Reed, Plainfield, IL (US);
Santanu Banerjee, Pune (IN); Anand Harbindu, Shahjahanpur (IN)

(73) Assignee: ECOLAB USA Inc., St. Paul, MN (US)

( * ) Notice: Subject to any disclaimer, the term of this patent is extended or adjusted under 35 U.S.C. 154(b) by 0 days.

(21) Appl. No.: 14/294,759

(22) Filed: Jun. 3, 2014

(65) Prior Publication Data
US 2015/0345031 A1  Dec. 3, 2015

(51) Int. Cl.
| | | |
|---|---|---|
| C23F 11/14 | (2006.01) |
| C23F 11/12 | (2006.01) |
| C23F 11/00 | (2006.01) |
| C07C 59/245 | (2006.01) |
| C07C 229/24 | (2006.01) |

(52) U.S. Cl.
CPC ............. *C23F 11/144* (2013.01); *C07C 59/245* (2013.01); *C07C 229/24* (2013.01); *C23F 11/00* (2013.01); *C23F 11/122* (2013.01); *C23F 11/124* (2013.01)

(58) Field of Classification Search
CPC .......... C23F 11/00; C23F 11/08; C23F 11/10; C23F 11/122; C23F 11/124; C23F 11/14; C23F 11/141; C23F 11/144; C23F 11/146; C07C 229/20; C07C 229/22; C07C 229/24; C07C 59/245
See application file for complete search history.

(56) References Cited

U.S. PATENT DOCUMENTS

| | | | |
|---|---|---|---|
| 3,929,874 A | 12/1975 | Beermann et al. | |
| 5,130,052 A * | 7/1992 | Kreh et al. | 252/387 |
| 5,139,702 A * | 8/1992 | Carter et al. | 252/392 |
| 5,147,555 A * | 9/1992 | Brown et al. | 210/698 |
| 5,183,590 A | 2/1993 | Carter et al. | |
| 5,344,590 A * | 9/1994 | Carter et al. | 210/698 |
| 5,616,278 A | 4/1997 | Carey et al. | |

(Continued)

FOREIGN PATENT DOCUMENTS

| | | |
|---|---|---|
| CN | 102391491 | 3/2012 |
| JP | 49030316 | 3/1974 |

(Continued)

OTHER PUBLICATIONS

Machine Translation of JP 2012-171976 A.*

(Continued)

*Primary Examiner* — Mark Kopec
*Assistant Examiner* — Matthew R Diaz
(74) *Attorney, Agent, or Firm* — Eric D. Babych; Brinks Gilson & Lione

(57) ABSTRACT

Corrosion inhibitors and methods for inhibiting or reducing corrosion of metallic surfaces are provided. A corrosion inhibitor composition may include a 3-alkylamino-2-hydroxysuccinic acid compound. A method of inhibiting corrosion of a metallic surface in an aqueous system includes the step of contacting the surface with an effective amount of a corrosion inhibitor composition. The corrosion inhibitor composition may include other components, such as zinc, and it may also exclude phosphorus.

14 Claims, 2 Drawing Sheets

(56) References Cited

U.S. PATENT DOCUMENTS

| | | | |
|---|---|---|---|
| 5,846,925 A * | 12/1998 | Wilson | C23C 18/40 510/361 |
| 5,871,691 A | 2/1999 | Carey et al. | |
| 6,346,648 B1 | 2/2002 | O'Lenick, Jr. | |
| 6,585,933 B1 | 7/2003 | Ehrhardt et al. | |
| 6,642,192 B1 | 11/2003 | O'Lenick, Jr. | |
| 7,087,569 B2 | 8/2006 | Lentsch et al. | |
| 7,135,448 B2 | 11/2006 | Lentsch et al. | |
| 7,196,045 B2 | 3/2007 | Lentsch et al. | |
| 7,524,803 B2 | 4/2009 | Lentsch et al. | |
| 7,759,299 B2 | 7/2010 | Smith et al. | |
| 7,858,574 B2 | 12/2010 | Smith et al. | |
| 8,021,493 B2 | 9/2011 | Smith et al. | |
| 8,021,607 B2 * | 9/2011 | Pierce et al. | 252/396 |
| 8,025,840 B2 * | 9/2011 | Crovetto et al. | 422/17 |
| 8,303,768 B2 | 11/2012 | Shevchenko et al. | |
| 2013/0161265 A1 | 6/2013 | Fox et al. | |
| 2013/0233796 A1 | 9/2013 | Rao et al. | |
| 2013/0233804 A1 | 9/2013 | Xie et al. | |

FOREIGN PATENT DOCUMENTS

| | | | |
|---|---|---|---|
| JP | 08-067659 | | 3/1996 |
| JP | 09-272895 | | 10/1997 |
| JP | 10-158226 | | 6/1998 |
| JP | 2000219662 | A * | 8/2000 |
| JP | 2011231059 | A * | 11/2011 |
| JP | 2012171976 | | 9/2012 |
| WO | WO 96/33953 | | 10/1996 |

OTHER PUBLICATIONS

Hauptmann, H. and Berl, H., "Reaction of trans-epoxysuccinic acid with ammonia and amines; β-hydroxyaspartic acid and its N-alkyl derivatives", Anais da Associacao Brasileira de Quimica (1960), 19, 173-83.

* cited by examiner

SPECIFIC 3-ALKYLAMINO-2-HYDROXYSUCCINIC ACIDS AND THEIR SALTS AS CORROSION INHIBITORS FOR FERROUS METALS

FIELD OF THE INVENTION

The present disclosure generally relates to corrosion control. More particularly, the disclosure pertains to the use of 3-alkylamino-2-hydroxysuccinic acid compositions to reduce or inhibit corrosion of metallic surfaces in aqueous systems.

DESCRIPTION OF THE RELATED ART

Carbon steel corrosion inhibition has evolved over many decades from the use of chromate to the current heavy metals and phosphate chemistries. Several decades ago, chromate was banned and was predominantly replaced by molybdenum, zinc, silicate and phosphate. Several advances have been made in the phosphate chemistries from the use of orthophosphate to polyphosphate and the use of organic phosphates, phosphonates, and phosphinates. Currently, phosphorus is under environmental pressure and may only be used in very low-level quantities.

Ferrous metals, such as carbon steel, are among the most commonly used structural materials in industrial systems. Loss of the metals from surfaces resulting from general corrosion causes deterioration of the structural integrity of the system or structure because of reduction of mechanical strength. Localized corrosion (e.g. pitting) may pose an even greater threat to the normal operation of the system than general corrosion because such corrosion will occur intensely in one particular location and may cause perforations in the system structure carrying an industrial water stream. These perforations may cause leaks which require shutdown of the entire industrial system so that repair can be made. Indeed, corrosion problems usually result in immense maintenance costs, as well as costs incurred as a result of equipment failure. Therefore, the inhibition of metal corrosion in industrial water is critical.

Corrosion protection of ferrous metals in industrial water systems is often achieved by adding a corrosion inhibitor. Many corrosion inhibitors, including chromate, molybdate, zinc, nitrite, orthophosphate, and polyphosphate have been used previously, alone or in combination, in various chemical treatment formulations. However, these inorganic chemicals can be toxic, detrimental to the environment, and/or not very effective against localized corrosion, especially at economically feasible and/or environmentally acceptable low dosage levels.

Corrosion has also been managed by using more corrosion-resistant materials, applying protective coatings, and/or using sacrificial anode or chemical treatment. Since aqueous corrosion has been shown to consist of, for most part, an electrochemical process, the chemical treatments have been applied as anodic inhibitors, cathodic inhibitors, or a combination of cathodic and anodic inhibitors.

BRIEF SUMMARY

The present disclosure relates to corrosion inhibitor compositions and methods for inhibiting corrosion. In one aspect, a corrosion inhibitor composition is provided comprising one or more members selected from the group consisting of 2-n-butylamino-3-hydroxysuccinic acid, 2-dimethylamino-3-hydroxysuccinic acid, 2-diethylamino-3-hydroxysuccinic acid, 2-isoamyamino-3-hydroxysuccinic acid, 2-ethylenediamino-3-hydroxysuccinic acid, 2-(2-methoxyethyl)amino-3-hydroxysuccinic acid, 2-(3-methoxypropyl)amino-3-hydroxysuccinic acid, 2-sec-butylamino-3-hydroxysuccinic acid, 2-dimethylamino-N-oxide-3-hydroxysuccinic acid, any salt thereof, and any combination thereof.

In another aspect, a corrosion inhibitor composition is provided comprising zinc and a 3-alkylamino-2-hydroxysuccinic acid compound.

In an additional aspect, a method of inhibiting corrosion of a metallic surface in an aqueous system is provided. The method comprises the step of contacting the metallic surface with an effective amount of a corrosion inhibitor composition, wherein the corrosion inhibitor composition comprises a 3-alkylamino-2-hydroxysuccinic acid compound and the effective amount is from about 1 ppm to about 500 ppm.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Figure 1:
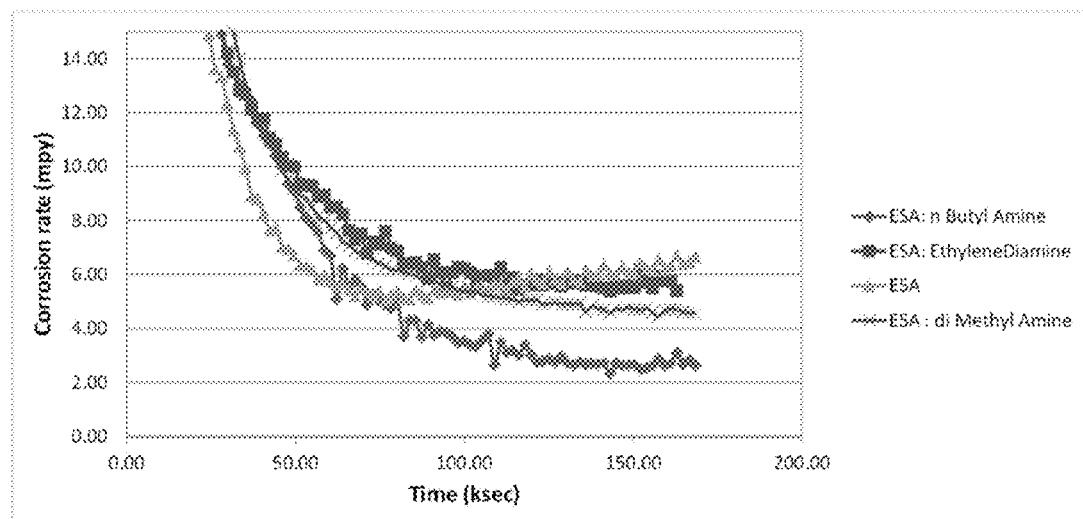
FIG. 1 shows a graphical analysis of the performance of certain corrosion inhibitor compositions.

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

The present disclosure relates to corrosion inhibitor compositions and various methods for inhibiting corrosion. The corrosion inhibitor compositions include epoxy succinates (ESA) and various derivatives thereof. The corrosion inhibitor compositions can effectively inhibit or prevent corrosion of surfaces comprising metals. In some aspects, the metals are ferrous metals, such as steel, iron, and alloys of iron with other metals, such as stainless steel. In certain aspects of the present disclosure, the corrosion inhibitor composition does not contain phosphorous or any heavy metal ions. The corrosion inhibitor composition may contain functionalities that enhance the corrosion inhibitor composition's affinity for metallic surfaces, such as surfaces comprising iron.

The presently disclosed corrosion inhibitor compositions show strong efficacy as corrosion inhibitors for surfaces comprising carbon steel metallurgy, ferrous metals, and the like. The corrosion inhibitor compositions can achieve a high level of corrosion inhibition without the use of chemistries containing phosphorus and such high levels of corrosion inhibition, such as less than 3 mpy, may also be achieved when using only a small amount of the presently disclosed corrosion inhibitor compositions.

In some aspects, the corrosion inhibitor composition comprises one or more 3-alkylamino-2-hydroxysuccinic acid compounds. Illustrative, non-limiting examples of 3-alkylamino-2-hydroxysuccinic acid compounds are selected from the group consisting of 2-n-butylamino-3-hydroxysuccinic acid, 2-dimethylamino-3-hydroxysuccinic acid, 2-diethylamino-3-hydroxysuccinic acid, 2-isoamyamino-3-hydroxysuccinic acid, 2-ethylenediamino-3-hydroxysuccinic acid, 2-(2-methoxyethyl)amino-3-hydroxysuccinic acid, 2-(3-methoxypropyl)amino-3-hydroxysuccinic acid, 2-sec-butylamino-3-hydroxysuccinic acid, 2-dimethylamino-N-oxide-3-hydroxysuccinic acid, and any combination thereof. The corrosion inhibitor composition may comprise any one of these 3-alkylamino-2-hydroxysuccinic acid compounds or it may comprise a mixture of any two or more of these 3-alkylamino-2-hydroxysuccinic acid compounds. In one embodiment, the corrosion inhibitor comprises 2-t-butoxide-3-hydroxysuccinic acid or a salt thereof. Additionally, the corrosion inhibitor composition may comprise a salt of any of the foregoing 3-alkylamino-2-hydroxysuccinic acid compounds. In addition, the corrosion inhibitor composition may be added to the system in a masked chemical form that will form the foregoing compositions when placed in water.

In general, the presently disclosed corrosion inhibitor compositions can be made using any of the known procedures in the art. For example, an amine, such as an alkyl amine, may be reacted with an ESA to form a corrosion inhibitor composition according to the present disclosure. As an illustrative example, butyl amine may be reacted disodium cis-epoxysuccinate in water at about 100° C. to form a corrosion inhibitor composition in accordance with the present disclosure. In certain aspects, the parent ESA molecule of the corrosion inhibitor composition does not contain nitrogen. Additional details regarding the synthesis of the presently disclosed corrosion inhibitor compositions may be found in the example section of the present application.

In some aspects of the present disclosure, the corrosion inhibitor composition excludes phosphorus. In certain aspects, the corrosion inhibitor composition may comprise additional inhibitors. An illustrative example of an additional inhibitor is zinc.

The zinc component may come from an inorganic salt which comprises zinc and/or the zinc component may come from an organic salt which comprises zinc. Illustrative, non-limiting examples of inorganic salts comprising zinc are zinc chloride, zinc nitrate, zinc nitrite, and zinc sulfate. Illustrative, non-limiting examples of organic salts comprising zinc are zinc acetate and zinc citrate. The present inventors have unexpectedly discovered a strong synergism between the presently disclosed corrosion inhibitor compositions and zinc, and this synergism is also expected to be achieved using the presently disclosed corrosion inhibitor compositions in combination with silicate, borate, aluminate, and/or phosphate.

In terms of the relative amounts of the corrosion inhibitor composition and the zinc when used together, a ratio of the corrosion inhibitor composition to zinc may be from about 15:1, about 12.5:1, about 10:1, about 7.5:1, about 4.5:1, about 1:1, or any ratio therebetween.

In some aspects, an effective amount, such as from about 1 ppm to about 500 ppm, of the corrosion inhibitor composition may be added to an aqueous system containing surfaces susceptible of corrosion. The surfaces may comprise carbon steel metallurgy, ferrous metals, and the like. The corrosion inhibitor composition may be added directly onto the surface or the corrosion inhibitor composition may be added to the water of an aqueous system which comprises the surface to be treated.

The effective amount is not limited and may be appropriately selected by one of ordinary skill in the art depending upon the particular aqueous system, the water chemistry, etc. In some aspects, the effective amount is from about 2 ppm to about 200 ppm. In other aspects, the effective amount is from about 5 to about 100 ppm. In still other aspects, the effective amount is less than about 35 ppm. In one particular aspect, the effective amount is about 10 ppm to about 25 ppm.

In certain aspects of the present disclosure, an effective amount of zinc may be added directly to the surface to be treated or it may be added to the aqueous system containing one or more surfaces susceptible of corrosion along with the corrosion inhibitor composition. Each component may be added separately or as a mixture and the addition may be manual addition or automatic addition using chemical injection pumps and the automated system described below. In some aspects, the effective amount of zinc is from about 0.5 ppm to about 10 ppm. In other aspects, the effective amount of zinc is from about 2 ppm to about 5 ppm.

In one particular aspect, zinc is added as about 2 ppm active zinc and a ratio of corrosion inhibitor composition to zinc is about 12.5:1 (i.e. about 25 ppm active corrosion inhibitor composition to about 2 ppm active zinc). Zinc may act as a cathodic corrosion inhibitor and corrosion inhibition may improve with higher amounts of zinc.

The presently disclosed corrosion inhibitor compositions may be used in any aqueous system comprising surfaces susceptible of corrosion. For example, the corrosion inhibitor compositions may be used in once-through, open loop, or closed loop recirculating cooling water systems. Other aqueous systems include, but are not limited to, systems used in petroleum production and oil recovery (e.g., well casing, transport pipelines, etc.) and refining, geothermal wells, and other oil field applications; boilers and boiler water systems; systems used in power generation, mineral process waters including mineral washing, flotation and benefaction; paper mill digesters, washers, bleach plants, white water systems and mill water systems; black liquor evaporators in the pulp industry; gas scrubbers and air washers; continuous casting processes in the metallurgical industry; air conditioning and refrigeration systems; building fire protection heating water, such as pasteurization water; water reclamation and purification systems; membrane filtration water systems; food processing streams and waste treatment systems as well as in clarifiers, liquid-solid applications, municipal sewage treatment systems; and industrial or municipal water distribution systems.

The presently disclosed corrosion inhibitor compositions may be used in connection with a biocide, such as an oxidizing biocide. Biocides are commonly used in aqueous systems and the presently disclosed corrosion inhibitor compositions show a surprising chemical stability in the presence of biocides, such as bleach.

In certain aspects, the presently disclosed corrosion inhibitor compositions may comprise one or more of the following characteristics:

Halogen stability up to about 0.5 ppm free residual chlorine (FRC);
Ability to handle water temperatures up to about 60° C.;

Compatibility with azoles, dispersants, and cooling water polymers;

Calcium tolerance up to about 500 ppm as $CaCO_3$;

Chloride tolerance up to about 600 ppm as Cl;

Stability over a pH from about 6 to about 9;

Low toxicity (e.g. $LC_{50}$>100 mg/L); and

Stable for a Holding Time Index (HTI) of from a few seconds (e.g. 30 seconds, 60 seconds, 90 seconds, etc.) up to about 250 hours.

In particular aspects of the present disclosure, the corrosion inhibitors may be used in connection with warewashing compositions. Warewashing compositions may be used for protecting articles, such as glassware or silverware, from corrosion in a dishwashing or warewashing machine. However, it is to be understood that the warewashing compositions comprising the presently disclosed corrosion inhibitors can be available for cleaning environments other than inside a dishwashing or warewashing machine.

The corrosion inhibitor composition may be included in the warewashing composition in an amount sufficient to provide a use solution that exhibits a rate of corrosion and/or etching of glass that is less than the rate of corrosion and/or etching of glass for an otherwise identical use solution, except for the absence of the corrosion inhibitor composition. In some aspects, the use solution may include at least about 6 ppm of the corrosion inhibitor composition. In other aspects, the use solution may include between about 6 ppm and about 300 ppm of the corrosion inhibitor composition. In still further aspects, the use solution may include between about 20 ppm and about 200 ppm of the corrosion inhibitor composition. In the case of a warewashing composition concentrate that is intended to be diluted to a use solution, it is expected that the corrosion inhibitor composition may be provided at a concentration of between about 0.5 wt. % and about 25 wt. %, and between about 1 wt. % and about 20 wt. % of the concentrate.

In addition to the corrosion inhibitor composition, the warewashing composition and/or use solution may also include cleaning agents, alkaline sources, surfactants, chelating/sequestering agents, bleaching agents, detergent builders or fillers, hardening agents or solubility modifiers, defoamers, anti-redeposition agents, threshold agents, aesthetic enhancing agents (i.e., dye, perfume), and the like. Adjuvants and other additive ingredients will vary according to the type of composition being manufactured. It should be understood that these additives are optional and need not be included in the cleaning composition. When they are included, they can be included in an amount that provides for the effectiveness of the particular type of component.

The presently disclosed corrosion inhibitors may be used in connection with any warewashing operation or any warewashing composition, such as those warewashing compositions disclosed in U.S. Pat. No. 7,196,045, U.S. Pat. No. 7,524,803, U.S. Pat. No. 7,135,448, U.S. Pat. No. 7,759,299, U.S. Pat. No. 7,087,569, U.S. Pat. No. 7,858,574, and U.S. Pat. No. 8,021,493, the entire contents of each of these patents being expressly incorporated into the present application.

Any of the presently disclosed aqueous systems may be automatically monitored and controlled. For example, the pH of the systems may be monitored and controlled or the amount of corrosion inhibitor composition in the aqueous system may be monitored and controlled. In certain aspects, the aqueous system may include a monitoring and controlling unit that comprises a controller device and a plurality of sensors. Each of the plurality of sensors may be configured to obtain a different characteristic of the water and each sensor may also be in communication with the controller. The plurality of sensors can comprise, for example, sensors for measuring conductivity, corrosion inhibitor concentration, pH, oxidation/reduction potential (ORP), fluorescence, biocide concentration, turbidity, temperature, flow, and dissolved oxygen (DO) in the water.

Based on signals received from the sensors, the controller may send signals to chemical injection pumps, which are in fluid communication with various chemicals, such as acids, bases, biocides, corrosion inhibitors, scale inhibitors, etc., to turn the pumps off (cause them to stop adding chemical) or turn them on (cause them to add a specified amount of more chemical). The components of this automated system may be in communication with each other in any number of ways, including, as illustrative examples, through any combination of wired connection, a wireless connection, electronically, cellularly, through infrared, satellite, or according to any other types of communication networks, topologies, protocols, and standards.

As used herein, the term "controller" or "controller device" refers to a manual operator or an electronic device having components such as a processor, memory device, digital storage medium, a communication interface including communication circuitry operable to support communications across any number of communication protocols and/or networks, a user interface (e.g., a graphical user interface that may include cathode ray tube, liquid crystal display, plasma display, touch screen, or other monitor), and/or other components. The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, internet connection, microwave link, infrared link, wired network (e.g., Ethernet) and the like. In addition, other components such as a signal conditioner or system monitor may be included to facilitate signal transmission and signal-processing algorithms.

The disclosed monitoring and controlling system provides methods to generate real-time, on-line, reliable data from the water of the industrial system. Based upon the data received by the controller from the plurality of sensors, real-time adjustments can be made to the water. For example, the plurality of sensors may provide continuous or intermittent feedback, feed-forward, or predictive information to the controller, which can relay this information to a relay device, such as the Nalco Global Gateway, which can transmit the information via cellular communications to a remote device, such as a cellular telephone, computer, or any other device that can receive cellular communications. This remote device can interpret the information and automatically send a signal (e.g. electronic instructions) back, through the relay device, to the controller to cause the controller to make certain adjustments to the output of the chemical injection pumps. The information may also be processed internally by the controller and the controller can automatically send signals to the pumps, to adjust the amount of chemical injection. Based upon the information received by the controller from the plurality of sensors or from the remote device, the controller can transmit signals to the various pumps to make automatic, real-time adjustments, to the amount of chemical that the pumps are injecting into the water of the system.

In certain aspects, the remote device or controller can include appropriate software to receive data from the plurality of sensors and determine if the data indicates that one or more measured properties of the water are within, or outside, an acceptable range. The software can also allow the controller or remote device to determine appropriate actions that should be taken to remedy the property that is outside of the acceptable range. The monitoring and controlling system and/or controller disclosed herein can incorporate programming logic to convert analyzer signals from the plurality of sensors to pump adjustment logic and, in certain embodiments, control one or more of a plurality of chemical injection pumps with a unique basis.

Data transmission of measured properties or signals to chemical pumps, alarms, remote monitoring devices, such as computers or cellular telephones, or other system components is accomplished using any suitable device, and across any number of wired and/or wireless networks, including as illustrative examples, WiFi, WiMAX, Ethernet, cable, digital subscriber line, Bluetooth, cellular technologies (e.g., 2G, 3G, Universal Mobile Telecommunications System (UMTS), GSM, Long Term Evolution (LTE), or more) etc. The Nalco Global Gateway is an example of a suitable device. Any suitable interface standard(s), such as an Ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used. As used herein, the term "network" encompasses all of these data transmission methods. Any of the described devices (e.g., archiving systems, data analysis stations, data capturing devices, process devices, remote monitoring devices, chemical injection pumps, etc.) may be connected to one another using the above-described or other suitable interface or connection.

Various additional automated methods that can be used in accordance with the present disclosure for monitoring and controlling industrial water systems are disclosed in U.S. Pat. No. 8,303,768, U.S. Patent Application Publication No. 2013/0161265, U.S. Patent Application Publication No. 2013/0233804, U.S. Patent Application Publication No. 2013/0233796, and U.S. Ser. No. 13/833,115, the contents of each of these documents being incorporated by reference into the present application in their entirety.

Examples

This example describes the synthesis of ESA and various adducts thereof with water soluble amines and amino acids viz. n-Butyl amine, cyclohexyl amine, L-aspartic acid, etc., and their application as corrosion inhibitors. Based on corrosion performance against mild steel, the n-butyl amine/epoxy succinate adduct was found to be the most effective among sixteen adducts screened.

Synthesis of Disodium cis-Epoxy succinate (ESA):

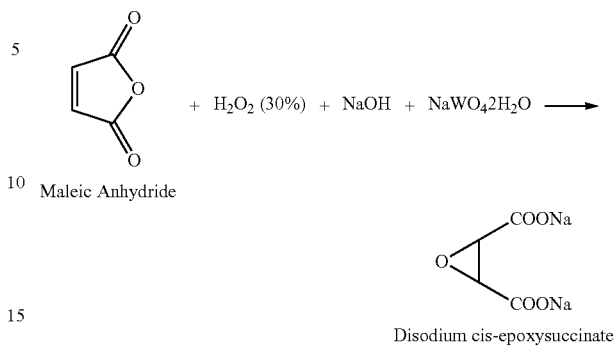

Maleic Anhydride

Disodium cis-epoxysuccinate

A 1-liter, 5-neck, round bottom flask equipped with stirrer, thermometer, and dropping funnel was charged with a filtered solution of 116 grams (1.0 mole) of maleic anhydride in 300 ml of distilled water. To this was added a solution of 60 grams (1.5 mole) of sodium hydroxide in 100 ml of water. The heat of neutralization caused a rise in temperature to about 70° C. To the warm solution was added 6.6 grams (0.02 mole) of sodium tungstate dihydrate, although similar experiments were performed using sodium molybdate and this reagent worked well and is also intended to be covered by the present disclosure. Standard pH electrodes were inserted into the solution and 1.2 mole of 30%, hydrogen peroxide was added in one portion. The strongly exothermic reaction was held at about 63 to 65° C. by cooling with an ice bath for about 15 minutes during which time the pH fell from about 5.5 to about 4.1. In order to maintain the pH at a minimum of 4, a solution of 0.5 mole of sodium hydroxide in 100 ml of water was added dropwise as needed throughout the remainder of the reaction. After an additional hour at 65° C., the solution was cooled to 40° C. and treated with the remainder of the sodium hydroxide solution. After vacuum concentration at 40° C., 176 grams (100%) of disodium cis-cis-Epoxy succinate was obtained as product.

Synthesis of Disodium cis-Epoxy succinate (ESA) adduct with amines and amino acids:

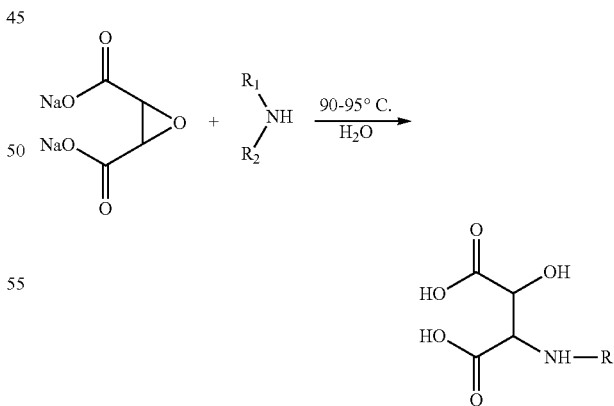

About 9.35 grams (1 mole) of cis-Epoxy succinate and (1 mole) of a respective amine were added to 25 ml of water at room temperature and the reaction vessel was closed. The mixture was refluxed, while stirring, for 12 hours, to 90 to 95° C. and reaction mixture was dried in a rotary evaporator to obtain the product.

TABLE 1

List of Hydrophilic amines and amino acid reactants, as well as ESA adduct product structures and yields (%):

| No. | Amine | Structure of product | Yield (%) |
|---|---|---|---|
| 1 | Ammonia (1:1 and 2:1) | (structure shown) | 88 (1:1)<br>81 (2:1) |
| 2 | Ethanolamine | (structure shown) | 78 |
| 3 | 2-Methoxy Ethyl Amine | (structure shown) | 81 |
| 4 | 3-Methoxy Propyl Amine | (structure shown) | 81 |
| 5 | Ethylene Diamine | (structure shown, NHCH2CH2NH2) | 83 |
| 6 | 1,3-Diaminopropane | (structure shown, NHCH$_2$CH$_2$CH$_2$NH$_2$) | 81 |
| 7 | iso-Butyl Amine | (structure shown) | 87 |

TABLE 1-continued
List of Hydrophilic amines and amino acid reactants, as well as ESA adduct product structures and yields (%):
| No. | Amine | Structure of product | Yield (%) |
|---|---|---|---|
| 8 | n-Butyl Amine | 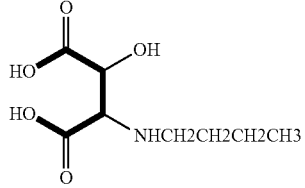 | 85 |
| 9 | sec-Butyl Amine | 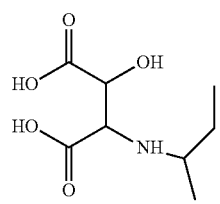 | 87 |
| 10 | Cyclo Hexyl Amine | 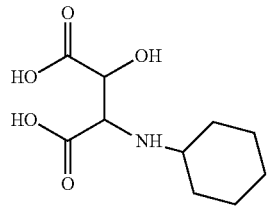 [SMILES: O=C(O)C(O)C(NC1CCCCC1)C(=O)O] | 86 |
| 11 | di-Butyl Amine | 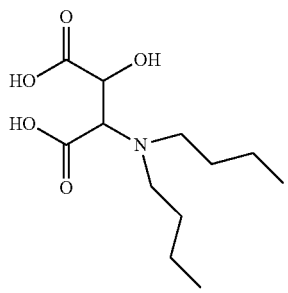 [SMILES: CCCCN(CCCC)C(C(=O)O)C(O)C(=O)O] | 65 |
| 12 | Methyl amine | 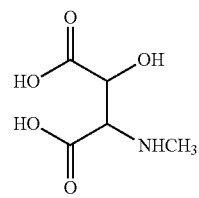 [SMILES: CNC(C(=O)O)C(O)C(=O)O] | 80 |
| 13 | L-Aspartic Acid | 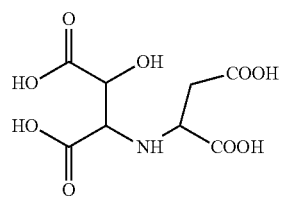 [SMILES: O=C(O)CC(NC(C(=O)O)C(O)C(=O)O)C(=O)O] | 75 |
| 14 | L-Glutamic Acid | 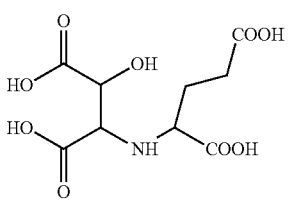 [SMILES: O=C(O)CCC(NC(C(=O)O)C(O)C(=O)O)C(=O)O] | 74 |

TABLE 1-continued

List of Hydrophilic amines and amino acid reactants, as well as ESA adduct product structures and yields (%):

| No. | Amine | Structure of product | Yield (%) |
|---|---|---|---|
| 15 | TRIS Buffer | *(structure)* | 72 |
| 16 | Di Methyl Amine | *(structure)* | 78 |
| 17 | Di Ethyl Amine | *(structure)* | 75 |
| 18 | Pyrrolidine | *(structure)* | 83 |
| 19 | 2-((2-aminoethyl)amino)ethanol | *(structure)* | 78 |
| 20 | 3,3'-(alkane-1,n-diylbis(azanediyl))bis (2-hydroxysuccinic acid) | *(structure)* where n = 0 to 100 | 70-80 |

Corrosion Study

The electrochemical corrosion study was carried out using the Gamry electrochemical corrosion measurement technique. The purpose of the corrosion measurement was to evaluate the performance of the synthesized corrosion inhibitor compositions against Carbon Steel Metallurgy corrosion inhibition.

Experimental conditions used during the corrosion inhibition experiment were:

a) Corrosion rate KPI<3 mpy for Carbon Steel Metallurgy;

b) Gamry Electrochemical Instrument and Pine Rotator;

c) 800 mL test solution into a 1 L glass cell;

d) Dosage of Inhibitor: about 25 ppm;

e) Mild Steel cylindrical coupon polished using 600SiC polishing paper;
f) No pre-passivation: unpassivated coupons were used directly after polishing;
g) Temperature: about 120° F. (50° C.);
h) pH=about 8.0; and
i) RPM of Pine Rotator: 500 rpm.

TABLE 2

ESA derivatives and their corrosion inhibition performance

| Inhibitor | Corrosion Rate after 48 hrs (mpy) |
|---|---|
| ESA | 5.10 |
| ESA: Ammonia (2:1) | 14.80 |
| ESA: 2- Methoxy Ethyl Amine | 10.50 |
| ESA: 3-Methoxy Propyl amine | 9.17 |
| ESA: Ethylene Diamine | 5.40 |
| ESA: 1,3-Diaminopropane | 9.55 |
| ESA: iso-Butyl amine | 11.90 |
| ESA: n-Butyl amine | 2.84 |
| ESA: sec-Butyl amine | 6.68 |
| ESA: Cyclo Hexyl amine | 13.30 |
| ESA: di-Butyl amine | 19.00 |
| ESA: L-Aspartic Acid | 7.11 |
| ESA: TRIS Buffer | 12.30 |
| ESA: Di Methyl Amine | 3.77 |
| ESA: Di Ethyl Amine | 8.85 |
| ESA: Pyrrolidine | 10.50 |
| ESA: 2-((2-aminoethyl) amino)ethanol | 7.61 |
| ESA: Iso Amyl Amine | 5.22 |

The carbon steel corrosion data for lead ESA derivatives are shown in FIG. 1. The parent ESA molecule showed corrosion rate up to <5 mpy in less than 24 hours with a steeper plot than the other derivatives, although the corrosion rate increases over time which indicates the possibility of ESA being converted to tartaric acid, which is not as good of a corrosion inhibitor. ESA: n Butyl Amine showed very good corrosion inhibition properties for carbon steel metallurgy which reached <5 mpy in less than 24 hours and then gradually decreased to <3 mpy over 48 hours, indicating a good inhibitor film formation. ESA showed a steeper decrease in corrosion rate over time, which indicates a faster film formation on metal surface by this molecule. ESA: n Butyl Amine showed a steady rate of film formation (slower than ESA), but the film grew most stable among the tested compositions. ESA: n Ethylene diamine also showed reasonably good corrosion inhibition for carbon steel metallurgy.

Blend of ESA: n Butyl Amine with Zinc

Figure 2:
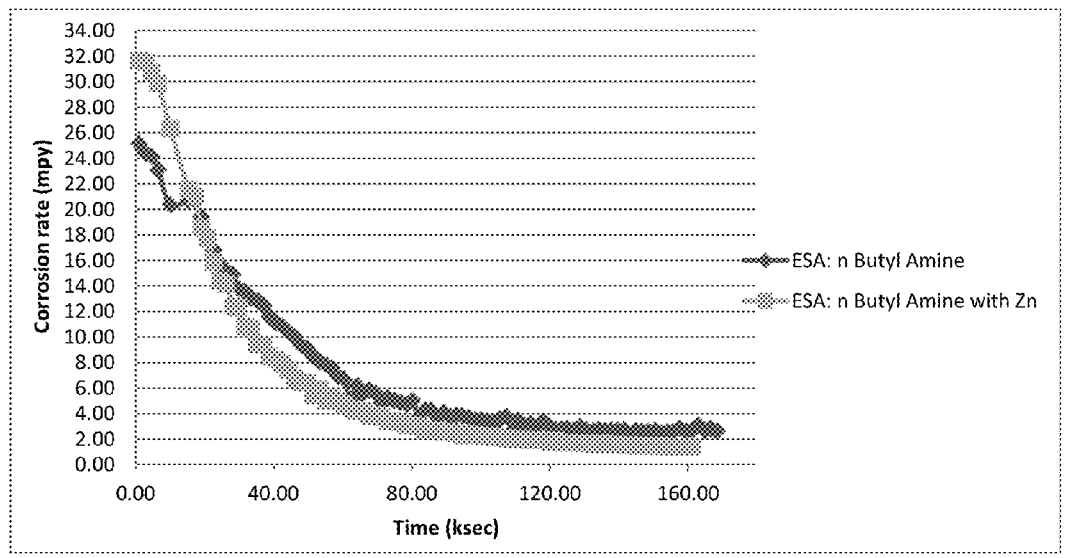
FIG. 2 shows a graphical analysis of the performance of a corrosion inhibitor composition by itself compared to the same corrosion inhibitor composition in combination with zinc.

Zinc is known to be a good cathodic corrosion inhibitor. The effect of blending zinc with one of the presently disclosed corrosion inhibitor compositions, ESA: n Butyl Amine, was studied to compare the performance against the corrosion inhibitor composition itself. The corrosion rate went below 3 mpy in less than 24 hours and the final value it reached was surprisingly and unexpectedly discovered to be 1.42 mpy, as can be seen in FIG. 2.

A number of other tests were performed in connection with certain presently disclosed corrosion inhibitor compositions as follows:

Bleach Stability Test: The cooling water application requires for the inhibitor to be stable against bleach dosing. The free chlorine tends to attack the organic molecules which in turn destroy the structural integrity, as well as corrosion resistant film, formed on the metal surface. In order to validate the stability of ESA: n Butyl Amine molecule in presence of bleach, bleach dosing was started after 24 hours of data collection using a Gamry instrument. The bleach solution was dosed manually to achieve 0.5-1 ppm FRC. Based on the total bleach consumption, the dosing rate was calculated, which was set for overnight continuous dosing. The molecule was observed to be bleach resistant in presence of up to 5 ppm of FRC at which point no significant loss in integrity of the corrosion resistant film was observed.

Calcium Tolerance Test: ESA: n Butyl Amine molecule was tested for its Calcium Tolerance by using different high calcium hardness containing solutions such as 500 ppm, 1000 ppm, and 10,000 ppm Ca as $CaCO_3$. The test was carried out at 60° C. and pH=10.2 at high calcium hardness using inhibitor dosages of 5-50 ppm actives, which did not show any change in turbidity due to addition of the inhibitor molecule.

Chloride Stability Test: The calcium tolerance test which used a solution of 100,000 ppm Ca as $CaCO_3$ had 7,100 ppm chloride as Cl. In the presence of such high chloride level, even the high dosage of the ESA: n Butyl Amine molecule did not show any change in turbidity, which in turn also confirms the chloride stability of this new inhibitor.

Temperature stability: The ESA: n Butyl Amine molecule was observed to be performing well at 60° C. which is the KPI for its temperature stability.

Calcium Carbonate Scale Inhibition: The ESA: n Butyl Amine molecule was tested for its Calcite scale inhibition efficiency. It was observed that for a 320× Calcite saturation index solution this molecule shows more than 90% threshold scale inhibition efficiency at a dosage of 1,500 ppm actives.

Copper Corrosion Inhibition: The ESA: n Butyl Amine molecule showed copper corrosion inhibition efficiency up to 0.2 mpy for an active dosage of 25 ppm.

Sea Water Scale Inhibition: Based on the benchscale test, ESA: n Butyl Amine showed good calcite scale inhibition efficiency at 25 ppm dosage as active at pH=8.60 using global average sea water chemistry.

The ESA: n Butyl Amine molecule was also subjected to stabilization tests for zinc, iron, and manganese ions. The presently disclosed corrosion inhibitor compositions, as exemplified by the ESA: n Butyl Amine molecule, are capable of stabilizing these metal ions, as can be seen in the following Tables:

TABLE 3

Zinc Stabilization

| ESA: n Butyl Amine Dose | Initial Zinc Concentration | Final Zinc Concentration After 4 Hours of Heating | Zinc Stabilization (%) |
|---|---|---|---|
| 25 ppm | 2.9 ppm | 2.69 ppm | 92.75% |
| 25 ppm | 5.8 ppm | 5.46 ppm | 94.14% |

TABLE 4

Iron Stabilization

| ESA: n Butyl Amine Dose | Initial Iron Concentration | Final Iron Concentration After 4 Hours of Heating | Final Iron Concentration in Blank | Stabilization (%) |
|---|---|---|---|---|
| 25 ppm | 1.98 ppm | 1.96 ppm | 1.91 ppm | 71.4% |
| 20 ppm | 1.98 ppm | 1.96 ppm | 1.91 ppm | 71.4% |

TABLE 5

Manganese Stabilization

| ESA: n Butyl Amine Dose | Initial Manganese Concentration | Final Manganese Concentration After 4 Hours of Heating | Final Manganese Concentration in Blank | Manganese Stabilization (%) |
|---|---|---|---|---|
| 25 ppm | 2.0 ppm | 1.8 ppm | 1.7 ppm | 68% |

In conclusion, the presently disclosed corrosion inhibitor compositions have been shown to be water soluble, possess advantageous properties as corrosion inhibitors, and may be synthesized in very good yields.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A corrosion inhibitor composition comprising zinc and one or more members selected from the group consisting of 2-ethylenediamino-3-hydroxysuccinic acid, 2-(2-methoxyethyl)amino-3-hydroxysuccinic acid, 2-(3-methoxypropyl)amino-3-hydroxysuccinic acid, 2-dimethylamino-N-oxide-3-hydroxysuccinic acid, any salt thereof, and any combination thereof.

2. The corrosion inhibitor composition of claim 1, wherein the composition excludes phosphorus.

3. The corrosion inhibitor composition of claim 1, wherein the composition comprises a salt of the one or more members selected.

4. The corrosion inhibitor composition of claim 1, wherein the zinc comprises an inorganic salt selected from the group consisting of zinc chloride, zinc nitrate, zinc nitrite, zinc sulfate, and any combination thereof.

5. The corrosion inhibitor composition of claim 1, wherein the zinc comprises an organic salt selected from the group consisting of zinc acetate, zinc citrate, and any combination thereof.

6. The corrosion inhibitor composition of claim 1, wherein a ratio of the one or more members selected to the zinc is about 12.5:1.

7. A method of inhibiting corrosion of a metallic surface in an aqueous system, comprising:
contacting the metallic surface with a corrosion inhibitor composition, wherein the corrosion inhibitor composition comprises an effective amount of zinc one or more members selected from the group consisting of 2-ethylenediamino-3-hydroxysuccinic acid, 2-(2-methoxyethyl)amino-3-hydroxysuccinic acid, 2-(3-methoxypropyl)amino-3-hydroxysuccinic acid, 2-dimethylamino-N-oxide-3-hydroxysuccinic acid, any salt thereof, and any combination thereof, the one or more members selected having an effective amount being from about 1 ppm to about 500 ppm.

8. The method of claim 7, wherein the effective amount of the one or more members selected is from about 2 ppm to about 200 ppm.

9. The method of claim 7, wherein the effective amount of the one or more members is less than about 35 ppm.

10. The method of claim 7, wherein the corrosion inhibitor composition excludes phosphorus.

11. The method of claim 7, wherein the effective amount of zinc is from about 0.5 ppm to about 10 ppm.

12. The method of claim 7, wherein a ratio of the one or more members selected to the zinc is about 12.5:1.

13. The method of claim 7, wherein the metallic surface comprises a ferrous metal.

14. The method of claim 7, wherein the aqueous system is selected from the group consisting of a once-through cooling water system, an open loop cooling water system, a closed loop cooling water system, a well casing, a transport pipeline, a boiler water system, a system used in power generation, a mineral processing water system, a paper mill digester, a washer, a bleach plant, a white water system, a mill water system, a black liquor evaporator, a gas scrubber, an air washer, a continuous casting system, an air conditioning system, a refrigeration system, a building fire protection water heating system, a pasteurization water system, a water reclamation system, a water purification system, a membrane filtration system, a food processing system, a waste treatment system, a sewage treatment system, a warewashing system, and a water distribution system.

\* \* \* \* \*